United States Patent [19]

Maurer et al.

[11] 4,215,132
[45] Jul. 29, 1980

[54] COMBATING ARTHROPODS WITH N,N-DIMETHYL-O-(3-SUBSTITUTED-PYRAZOL-5-YL)-CARBAMIC ACID ESTERS

[75] Inventors: Fritz Maurer, Wuppertal; Hans-Jochem Riebel, Selters; Rolf Schröder, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 31,096

[22] Filed: Apr. 18, 1979

[30] Foreign Application Priority Data

May 6, 1978 [DE] Fed. Rep. of Germany ....... 2819932

[51] Int. Cl.² .................. C07D 231/20; A01N 9/22
[52] U.S. Cl. .................. 424/273 P; 548/377; 548/367
[58] Field of Search ................ 548/377; 424/273 P

[56] References Cited

U.S. PATENT DOCUMENTS 3,449,502  6/1969  Gubler ........................ 548/377
4,126,690  11/1978  Maurer et al. ................ 548/377

OTHER PUBLICATIONS

Kay et al., J. Chem. Soc. 1970, C(3), pp. 445–448.

*Primary Examiner*—Alan L. Rotman
*Assistant Examiner*—Natalia Harkaway
*Attorney, Agent, or Firm*—Sprung, Felfe, Horn, Lynch & Kramer

[57] ABSTRACT

N,N-dimethyl-O-(3-substituted-pyrazol-5-yl)-carbamic acid esters of the formula

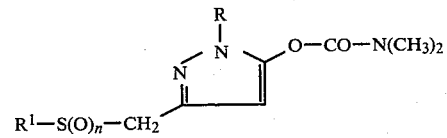

in which
R is hydrogen or optionally substituted alkyl,
R¹ is alkyl, and
n is 1 or 2,
which possess arthropodicidal properties.

9 Claims, No Drawings

COMBATING ARTHROPODS WITH N,N-DIMETHYL-O-(3-SUBSTITUTED-PYRAZOL-5-YL)-CARBAMIC ACID ESTERS

The present invention relates to and has for its objects the provision of particular new N,N-dimethyl-O-(3-substituted-pyrazol-5-yl)-carbamic acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that N,N-dimethyl-O-pyrazolyl-carbamic acid esters, for example N,N-dimethyl-O-(1-phenyl-3-methyl-pyrazol-5-yl)- and N,N-dimethyl-O-(1-iso-propyl-3-methyl-pyrazol-5-yl)-carbamic acid ester, have insecticidal properties (see Swiss Pat. No. 279,553; Chem. Abstracts 47 (1953), 10172 a).

The present invention now provides, as new compounds, the N,N-dimethyl-O-pyrazolylcarbamic acid esters of the general formula

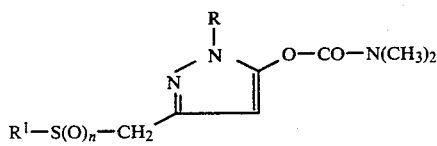

in which
R represents hydrogen or optionally substituted alkyl,
R$^1$ represents alkyl and
n represents 1 or 2.

The new compounds are distinguished by a powerful insecticidal activity.

Preferably, R represents hydrogen, straight-chain or branched alkyl with 1 to 8 (especially 1 to 5) carbon atoms or cyanoethyl, R$^1$ represents straight-chain alkyl with 1 to 5 (especially 1 to 3) carbon atoms and n represents 1 to 2.

Surprisingly, the N,N-dimethyl-O-pyrazolyl-carbamic acid esters according to the invention exhibit a better insecticidal action than the corresponding compounds, already known from the state of the art, of analogous structure and the same type of action. The products according to the present invention thus represent a true enrichment of the art.

The invention also provides a process for the preparation of an N,N-dimethyl-O-pyrazolyl-carbamic acid ester of formula (I) in which
(a) an hydroxy-pyrazole of the general formula

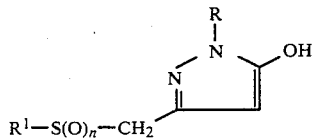

wherein
R, R$^1$ and n have the meanings stated above,
is reacted with an N,N-dimethylcarbamic acid halide of the general formula $$Hal-Co-N(CH_3)_2 \quad (III),$$

wherein
Hal represents chlorine or bromine,
if appropriate in the presence of an acid acceptor and if appropriate in the presence of a diluent, or (b) an hydroxypyrazole of the general formula (II) above, wherein
R, R$^1$ and n have the meanings stated above,
is reacted with phosgene and the product is then reacted with dimethylamine, if appropriate in the presence of an acid acceptor and if appropriate in the presence of a diluent, or (c) an N,N-dimethyl-O-pyrazol-5-yl-carbamic acid ester of the general formula (I), wherein,
R and R$^1$ have the meanings stated above but
n represents zero,
is reacted with the equimolar amount of the oxidizing agent hydrogen peroxide, if appropriate in the presence of a diluent, or (d) an N,N-dimethyl-O-pyrazol-5-yl-carbamic acid ester of the formula (I), wherein
R and R$^1$ have the meanings stated above but
n represents zero,
is reacted with at least two equivalents of the oxidizing agent m-chloro-perbenzoic acid, if appropriate in the presence of a diluent.

If 1-methyl-3-ethylsulphinyl-methyl-5-hydroxy-pyrazole and N,N-dimethyl-carbamic acid chloride are used as starting substances according to process variant (a), 1-tert.-butyl-3-methylsulphinyl-methyl-5-hydroxy-pyrazole, phosgene and dimethylamine are used as starting substances according to process variant (b), N,N-dimethyl-O-(1-methyl-3-ethylthiomethylpyrazol-5-yl)-carbamic acid ester and hydrogen peroxide are used as starting substances according to process variant (c) and N,N-dimethyl-O-(1-propyl-3-ethylthiomethyl-pyrazol-5-yl)-carbamic acid ester and m-chloro-perbenzoic acid are used as starting substances according to process variant (d), the course of the reactions can be represented by the equations which follow:

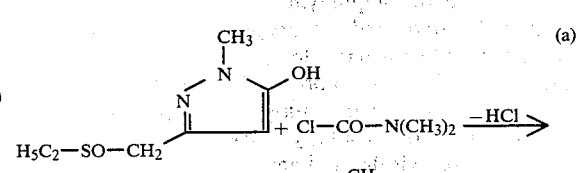

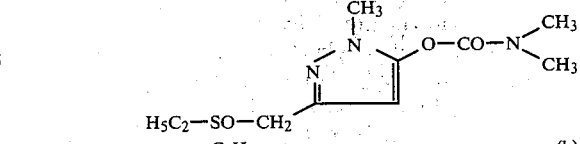

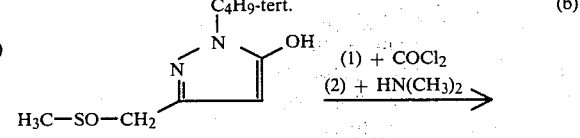

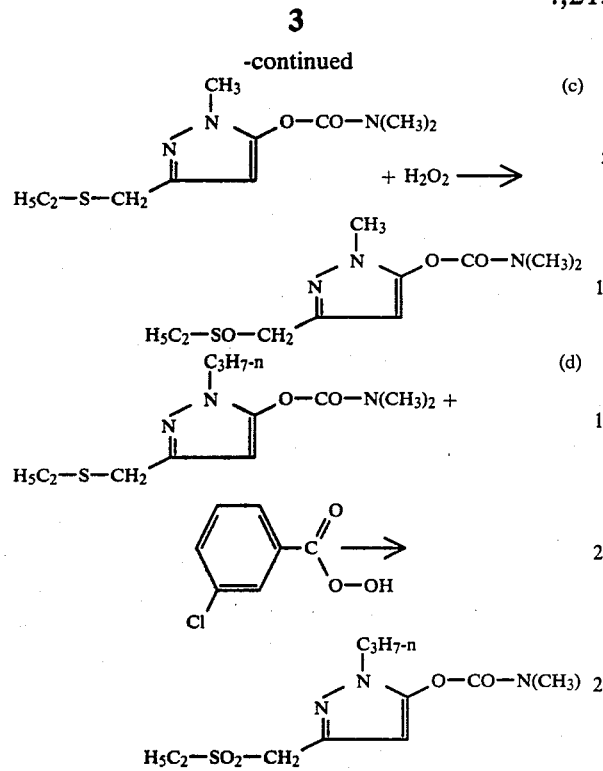

The hydroxy-pyrazoles of the formula (II) are obtained by reacting hydrazine or hydrazine derivatives with γ-alkylthioacetoacetic acid esters at 0° to 40° C. in inert diluents and then oxidizing the 3-alkylthiomethyl-5-hydroxy-pyrazoles thereby obtained, with hydrogen peroxide or m-chloroperbenzoic acid, likewise at 0° to 40° C. and likewise in the presence of diluents.

Examples which may be mentioned of the hydroxypyrazoles (II) to be used according to the invention are: 3-methylsulphinylmethyl-, 3-ethylsulphinylmethyl- and 3-n-propylsulphinylmethyl-5-hydroxy-pyrazole, 1-methyl-3-methylsulphinylmethyl-, 1-methyl-3-ethylsulphinylmethyl- and 1-methyl-3-n-propyl-sulphinylmethyl-5-hydroxy-pyrazole, 1-ethyl-3-methylsulphinylmethyl-, 1-ethyl-3-ethylsulphinylmethyl- and 1-ethyl-3-n-propyl-sulphinylmethyl-5-hydroxy-pyrazole, 1-n-pyropyl-3-methylsulphinylmethyl-, 1-n-propyl-3-ethylsulphinylmethyl- and 1-n-propyl-3-n-propyl-sulphinylmethyl-5-hydroxy-pyrazole, 1-iso-propyl-3-methylsulphinylmethyl-, 1-iso-propyl-3-ethylsulphinylmethyl- and 1-iso-propyl-3-n-propyl-sulphinylmethyl-5-hydroxy-pyrazole, 1-n-butyl-3-methylsulphinylmethyl-, 1-n-butyl-3-ethylsulphinylmethyl- and 1-n-butyl-3-n-propyl-sulphinylmethyl-5-hydroxy-pyrazole, 1-iso-butyl-3-methylsulphinylmethyl-, 1-iso-butyl-3-ethylsulphinylmethyl- and 1-iso-butyl-3-n-propyl-sulphinylmethyl-5-hydroxy-pyrazole, 1-sec.-butyl-3-methylsulphinylmethyl-, 1-sec.-butyl-3-ethylsulphinylmethyl- and 1-sec.-buty-3-n-propyl-sulphinylmethyl-5-hydroxy-pyrazole, 1-n-amyl-3-methylsulphinylmethyl-, 1-n-amyl-3-ethylsulphinylmethyl- and 1-n-amyl-3-n-propyl-sulphinylmethyl-5-hydroxy-pyrazole, 1-iso-amyl-3-methylsulphinylmethyl-, 1-iso-amyl-3-ethylsulphinylmethyl- and 1-iso-amyl-3-n-propyl-sulphinylmethyl-5-hydroxy-pyrazole, 1-sec.-amyl-3-methylsulphinylmethyl-, 1-sec.-amyl-3-ethylsulphinylmethyl- and 1-sec.-amyl-3-n-propyl-sulphinylmethyl-5-hydroxy-pyrazole and 1-(2-cyano-ethyl)-3-methylsulphinylmethyl-, 1-(2-cyano-ethyl)-3-ethylsulphinylmethyl- and 1-(2-cyano-ethyl)-3-n-propylsulphinylmethyl-5-hydroxy-pyrazole.

N,N-Dimethyl-carbamic acid chloride, which can be prepared by processes known from the literature and is frequently used industrially, is preferably employed as the carbamic acid halide of the formula (III) in process variant (a).

The N,N-dimethyl-O-(3-alkylthiomethylpyrazol-5-yl)-carbamic acid esters to be employed as starting substances in process variants (c) and (d) are defined by formula (I), but with the proviso that n represents zero. They can be prepared by a process analogous to process variant (a), from the corresponding 3-alkylthiomethyl-5-hydroxy-pyrazoles and N,N-dimehthyl-carbamic acid chloride.

Examples which may be mentioned of starting materials for variants (c) and (d) are: O-(1-methyl-3-methylthiomethyl-pryazole-5-yl)-, O-(1-methyl-3-ethylthiomethyl-pyrazol-5-yl)-, O-(1-methyl-3-n-propylthiomethyl-pyrazol- 5-yl)-, O-(1-ethyl-3-methylthiomethyl-pyrazol-5-yl)-, O-(1-ethyl-3-ethylthiomethyl-pyrazol-5-yl)-, O-(1-ethyl-3-n-propylthiomethyl-pyrazol-5-yl)-, O-(1-n-propyl-3-methylthiomethyl-pyrazol-5-yl)-, O-(1-n-propyl-3-ethylthiomethyl-pyrazol-5-yl)-, O-(1-n-propyl-3-n-propylthiomethyl-pyrazol-5-yl)-, O-(1-iso-propyl-3-methylthiomethyl-pyrazol-5-yl)-, O-(1-iso-propyl-3-ethylthiomethyl-pyrazol-5-yl)-, O-(1-iso-propyl-3-n-propylthiomethyl-pyrazol-5-yl)-, O-(1-n-butyl-3-methylthiomethyl-pyrazol-5-yl)-, O-(1-n-butyl-3-ethylthiomethyl-pyrazol-5-yl)-, O-(1-n-butyl-3-n-propylthiomethylpyrazol-5-yl)-, O-(1-iso-butyl-3-methylthiomethyl-pyrazol-5-yl)-, O-(1-iso-butyl-3-ethylthiomethyl-pyrazol-5-yl)-, O-(1-iso-butyl-3-n-propylthiomethyl-pyrazol-5-yl)-, O-(1-sec.-butyl-3-methylthiomethyl-pyrazol-5-yl)-, O-(1-sec.-butyl-3-ethylthiomethyl-pyrazol-5-yl)-, O-(1-sec.-butyl-3-n-propylthiomethyl-pyrazol-5-yl)-, O-(1-n-amyl-3-methylthiomethylpyrazol-5-yl)-, O-(1-n-amyl-3-ethylthiomethyl-pyrazol-5-yl)-, O-(1-n-amyl-3-n-propylthiomethyl-pyrazol-5-yl)-, O-(1-iso-amyl-3-methylthiomethyl-pyrazol-5-yl)-, O-(1-iso-amyl-3-ethylthiomethyl-pyrazol-5-yl)-, O-(1-iso-amyl-3-n-propylthiomethyl-pyrazol-5-yl)-, O-(1-sec.-amyl-3-methylthiomethyl-pyrazol-5-yl)-, O-(1-sec.-amyl-3-ethylthiomethyl-pyrazol-5-yl)-, O-(1-sec.-amyl-3-n-propylthiomethyl-pyrazol-5-yl)-, O-(1-(2-cyano-ethyl)-3-methylthiomethyl-pyrazol-5-yl)-, O-(1-(2-cyano-ethyl)-3-ethylthiomethyl-pyrazol-5-yl)-O-(1-(2-cyano-ethyl)-3-n-propyl-thiomethyl-pyrazol-5-yl)-, O-(3-methylthiomethyl-pyrazol-5-yl)-, O-(3-ethylthiomethylpyrazol-5-yl)- and O-(3-n-propylthiomethyl-pyrazol-5-yl)-N,N-dimethyl-carbamic acid ester.

The oxidizing agents hydrogen peroxide and m-chloroperbenzoic acid used in process variants (c) and (d) are generally known compounds and can be prepared by processes known from the literature.

Process variants (a), (b), (c) and (d) for the preparation of the new N,N-dimethyl-O-pyrazolyl-carbamic acid esters are preferably carried out using diluents. Virtually any inert organic solvent is a possible diluent. Preferred solvents include aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Aliphatic carboxylic acids, for example acetic acid, are preferred solvents for process (c).

Process variants (a) and (b) are preferably carried out using an acid acceptor. All the customary acid-binding agents can be used as the acid acceptors. Acid-binding agents which have proved particularly suitable are alkali metal carbonates and alcoholates, such as sodium carbonate and potassium carbonate and sodium methylate and ethylate and potassium methylate and ethylate, and furthermore aliphatic, aromatic or heterocyclic amines, for example triethylamine, trimethylamine, dimethylaniline, dimethylbenzylamine and pyridine.

In general, the process variants according to the invention are carried out at temperatures between 0° and 80° C. The range between 20° and 60° C. is preferred for process variant (a) and the range between 5° and 25° C. is preferred for process variants (b), (c) and (d).

In general, the reactions are carried out under normal pressure.

The starting substances are usually employed in equimolar amounts for carrying out process variants (a) and (b). An excess of one or the other of the reactants provides no substantial advantages. In general, the reaction is carried out in a suitable diluent in the presence of an acid acceptor. When the reaction has ended, the mixture is poured into water and extracted by shaking with an organic solvent, for example toluene. The organic phase is then worked up in the customary manner, by washing, drying and distilling off the solvent.

The reactants are likewise preferably employed in equimolar amounts in process variant (c). When the reaction has ended, the acetic acid used as a rule as the diluent in this process is distilled off in vacuo. Thereafter, an organic solvent, for example methylene chloride, is added to the residue and the organic phase is worked up in the customary manner by washing, drying and distilling off the solvent.

In process variant (d), the m-chloro-perbenzoic acid used as the oxidizing agent is usually employed in excess, and in particular between 2 and 3 moles are employed per mole of O-(3-alkylthiomethyl-pyrazol-5-yl)-N,N-dimethylcarbamic acid ester. The reaction is usually carried out in a water-immiscible solvent. The mixture is then washed until neutral and worked up as described for process variants (a) and (c).

Some of the new compounds are obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. The refractive index is used for their characterization.

If, after distilling off the solvent, the new products are obtained in the solid form, they are purified by recrystallization. The melting point is used for their characterization.

As already mentioned, the N,N-dimethyl-O-pyrazolylcarbamic acid esters according to the invention are distinguished by an outstanding insecticidal action.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentials* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabacia, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cocoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenbrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods, especially insects, which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of a compound according to the present invention, in admixture with a diluent or carrier.

The preparation of the novel compounds is shown in the following illustrative examples:

EXAMPLE 1

(a) The substituted 5-hydroxypyrazoles to be used as starting materials could be prepared, for example, as follows:

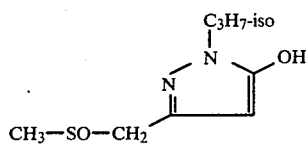

1st stage:

A solution of 0.11 mol of sodium methylate in methanol was added to a solution of 13.6 g (0.11 mol) of iso-propylhydrazine sulphate in 30 ml of methanol, while cooling. 17.6 g (0.1 mol) of γ-methylthioacetoacetic acid ethyl ester were then added to the mixture at room temperature and the mixture was subsequently stirred for 6 hours. The solvent was then distilled off in vacuo, the residue was triturated with water and, after crystallization, the crystals were filtered off. 13.4 g (73% of theory) of 1-isopropyl-3-methylthiomethyl-5-hydroxypyrazole were thus obtained.

2nd stage:

13.6 g (0.2 mol) of 50% strength hydrogen peroxide were added to a solution of 27.2 g (0.2 mol) of the above compound in 150 ml of glacial acetic acid at 5–10° C. The mixture was subsequently stirred at room temperature for 4 hours and the solvent was distilled off in vacuo. The residue was triturated with ether and, after crystallization, the crystals were filtered off. 25.8 g (64% of theory) of 1-isopropyl-3-methylsulphinylmethyl-5-hydroxy-pyrazole were obtained in this manner in the form of a pink-colored powder with a melting point of 117° C.

The following compounds of the formula

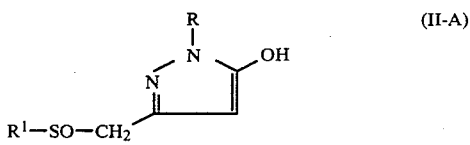

could be prepared in an analogous manner:

| Starting Material | R | R$^1$ | Yield (% of theory) | Melting point (°C.) |
|---|---|---|---|---|
| b | C$_4$H$_9$-iso | CH$_3$ | 39 | 114 |
| c | C$_4$H$_9$-n | CH$_3$ | 44 | 89 |
| d | CH$_3$ | n-C$_3$H$_7$ | 98 | 103 |
| e | H | CH$_3$ | 87 | 160 |

| Starting Material | R | R$^1$ | Yield (% of theory) | Melting point (°C.) |
|---|---|---|---|---|
| f | CH$_2$—CH$_2$—CN | CH$_3$ | 56 | 58 |

(b)

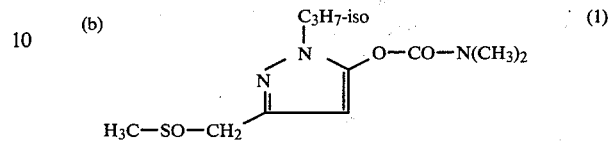

A suspension of 10.1 g (50 mmol) of 1-iso-propyl-3-methyl-sulphinylmethyl-5-hydroxy-pyrazole, 8.4 g (60 mmol) of ground potassium carbonate and 200 ml of acetonitrile was stirred at 50° C. for one hour and then cooled to room temperature and 5.4 g (50 mmol) of N,N-dimethyl-carbamic acid chloride were added. After stirring the reaction solution at 50° C. for one hour, 200 ml of water were added and the mixture was extracted by shaking with 200 ml of toluene. The organic phase was dried over magnesium sulphate and filtered and the solvent was stripped off from the filtrate in vacuo in a rotary evaporator. 11.8 g (87% of theory) of N,N-dimethyl-O-(1-iso-propyl-3-methylsulphinyl-methyl-pyrazol-5-yl)-carbamic acid ester remained in the form of pale violet crystals with a melting point of 69° C.

EXAMPLE 2

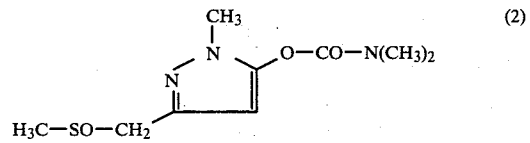

3.4 g (0.05 mol) of 50% strength hydrogen peroxide were added to a solution of 11.5 g (0.05 mol) of N,N-dimethyl-O-(1-methyl-3-methylthiomethyl-pyrazol-5-yl)-carbamic acid ester in 50 ml of glacial acetic acid at 5–10° C. The mixture was subsequently stirred at room temperature for 6 hours and the solvent was then distilled off in vacuo. The residue was dissolved in 100 ml of methylene chloride and the solution was washed with a solution of 10 g of potassium carbonate in 15 ml of water. The organic phase was separated off and dried over sodium sulphate. The solvent was then distilled off in vacuo. 12 g (98% of theory) of N,N-dimethyl-O-(1-methyl-3-methyl-sulphinylmethyl-pyrazol-5-yl)-carbamic acid ester were thus obtained in the form of a brown oil with a refractive index $n_D^{21}$ of 1.5362.

EXAMPLE 3

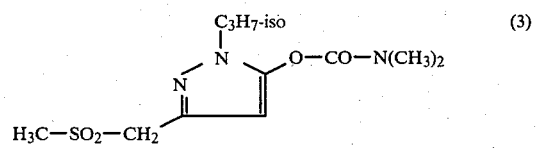

A solution of 21.3 g of m-chloroperbenzoic acid in 150 ml of chloroform was added dropwise to a solution of 12.9 g (0.05 mol) of N,N-dimethyl-O-(1-iso-propyl-3-methylthiomethyl-pyrazol-5-yl)-carbamic acid ester in 50 ml of chloroform at 5° C. The mixture was subsequently stirred at room temperature overnight and then filtered. The filtrate was washed with 10 ml of concentrated potassium carbonate solution and dried over sodium sulphate. The solvent was then stripped off in vacuo. 13 g (90% of theory) of N,N-dimethyl-O-(1-isopropyl-3-methylsulphonylmethyl-pyrazol-5-yl)-carbamic acid ester remained in the form of beige crystals with a melting point of 102° C.

The following compounds of the formula

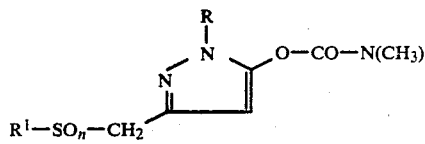

were each prepared analogously to one of Examples 1 to 3:

| Compound No. | R | R$^1$ | n | Yield (% of theory) | Physical data (Refractive index; melting point °C.) |
| --- | --- | --- | --- | --- | --- |
| 4 | C$_4$H$_9$-iso | CH$_3$ | 1 | 95 | $n_D^{21}$:1.5198 |
| 5 | C$_4$H$_9$-n | CH$_3$ | 1 | 91 | $n_D^{21}$:1.5209 |
| 6 | C$_3$H$_7$-iso | C$_2$H$_5$ | 1 | 70 | 82 |
| 7 | C$_4$H$_9$-sec. | CH$_3$ | 1 | 77 | $n_D^{20}$:1.5042 |
| 8 | C$_2$H$_5$ | CH$_3$ | 1 | 87 | $n_D^{20}$:1.5107 |
| 9 | CH(C$_2$H$_5$)$_2$ | CH$_3$ | 1 | 76 | $n_D^{20}$:1.5084 |
| 10 | C$_2$H$_5$ | C$_2$H$_5$ | 1 | 87 | $n_D^{20}$:1.5272 |
| 11 | C$_2$H$_5$ | C$_2$H$_5$ | 2 | 60 | 69 |
| 12 | CH$_3$ | CH$_3$ | 2 | 90 | 123 |
| 13 | C$_3$H$_7$-iso | C$_2$H$_5$ | 2 | 94 | 79 |
| 14 | CH$_3$ | n-C$_3$H$_7$ | 1 | 88 | $n_D^{20}$:1.5252 |
| 15 | H | CH$_3$ | 1 | 61 | 80 |
| 16 | CH$_2$—CH$_2$—CN | CH$_3$ | 1 | 69 | $n_D^{20}$:1.4973 |
| 17 | CH$_2$—CH$_2$—CN | C$_2$H$_5$ | 1 | 50 | $n_D^{20}$:1.5304 |
| 18 | CH$_2$—CH$_2$—CN | CH$_3$ | 2 | 85 | 102 |
| 19 | C$_2$H$_5$ | CH$_3$ | 2 | 85 | 82 |
| 20 | C$_4$H$_9$-sek. | CH$_3$ | 2 | 96 | $n_D^{20}$:1.5028 |
| 21 | CH(C$_2$H$_5$)$_2$ | CH$_3$ | 2 | | |
| 22 | C$_4$H$_9$-iso | CH$_3$ | 2 | 61 | 94 |
| 23 | C$_4$H$_9$-n | CH$_3$ | 2 | 66 | 61 |
| 24 | C$_4$H$_9$-tert. | CH$_3$ | 1 | | |
| 25 | C$_4$H$_9$-tert. | CH$_3$ | 2 | | |
| 26 | C$_3$H$_7$-n | CH$_3$ | 1 | | |
| 27 | C$_3$H$_7$-n | CH$_3$ | 2 | | |

The insecticidal activity of the compounds of this invention is illustrated by the following examples wherein the compounds according to the present invention are each identified by the number (given in brackets) from the preparative examples hereinabove.

EXAMPLE 4

Myzus test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica cleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared to the prior art: (2), (14), (8), (10), (3), (1), (6), (5), (4), (7), (16) and (9).

EXAMPLE 5

Critical concentration test/root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm(=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1), (2), (4), (5), (6) and (14).

EXAMPLE 6

Critical concentration test/root-systemic action
Test insect: *Phaedon cochleariae larvae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1) and (6).

It will be appreciated that the instant specification and examples are set forth by way of illustration and not limitation, and that various modifications and changes may be made without departing from the spirit and scope of the present invention.

What is claimed is:

1. An N,N-dimethyl-O-(3-substituted- pyrazol-5-yl)-carbamic acid ester of the formula

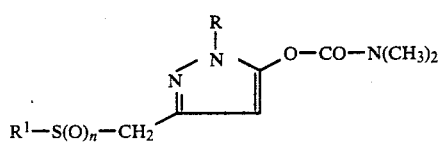

in which

R is hydrogen, alkyl with 1 to 8 carbon atoms or cyanoethyl, $R^1$ is alkyl with 1 to 5 carbon atoms, and n is 1 or 2.

2. A compound according to claim 1, wherein such compound is N,N-dimethyl-O-(1-iso-propyl-3-methyl-sulphinylmethyl-pyrazol-5-yl)-carbamic acid ester of the formula

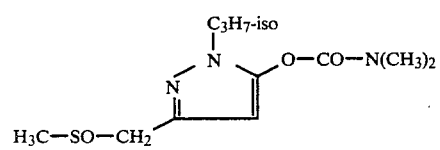

3. A compound according to claim 1, wherein such compound is N,N-dimethyl-O-(1-iso-propyl-3-methyl-sulphonyl-methyl-pyrazol-5-yl)-carbamic acid ester of the formula

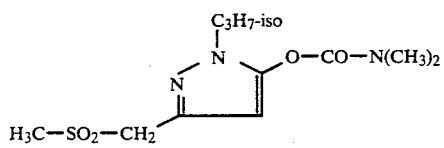

4. A compound according to claim 1, wherein such compound is N,N-dimethyl-O-(1-iso-propyl-3-ethyl-sulphinylmethyl-pyrazol-5-yl)-carbamic acid ester of the formula

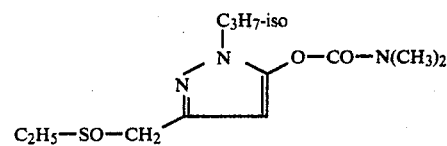

5. A compound according to claim 1, wherein such compound is N,N-dimethyl-O-(1-ethyl-3-methyl-sulphinyl-methylpyrazol-5-yl)-carbamic acid ester of the formula

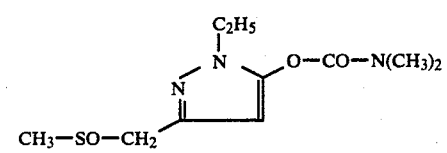

6. A compound according to claim 1, wherein such compound is N,N-dimethyl-O-(1-iso-propyl-3-ethyl-sulphonylmethyl-pyrazol-5-yl)-carbamic acid ester of the formula

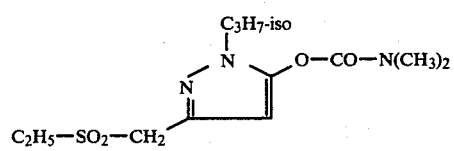

7. An arthropodicidal composition containing as active ingredient an arthropodicidally effective amount of a compound according to claim 1 in admixture with a diluent.

8. A method of combating arthropods which comprises applying to the arthropods, or to a habitat thereof, an arthropodicidally effective amount of a compound according to claim 1.

9. The method according to claim 8, wherein such compound is
N,N-dimethyl-O-(1-iso-propyl-3-methyl-sulphinyl-methyl-pyrazol-5-yl)-carbamic acid ester,
N,N,-dimethyl-O-(1-iso-propyl-3-methyl-sulphonyl-methyl-pyrazol-5-yl)-carbamic acid ester,
N,N,-dimethyl-O-(1-iso-propyl-3-ethyl-sulphinylmethyl-pyrazol-5-yl)-carbamic acid ester,
N,N,-dimethyl-O-(1-ethyl-3-methyl-sulphinyl-methyl-pyrazol-5-yl)-carbamic acid ester, or
N,N,-dimethyl-O-(1-iso-propyl-3-ethyl-sulphonylmethyl-pyrazol-5-yl)-carbamic acid ester.

* * * * *